US006990846B2

(12) United States Patent
Sioutas

(10) Patent No.: US 6,990,846 B2
(45) Date of Patent: *Jan. 31, 2006

(54) IMPACTOR INLET

(75) Inventor: Constantinos Sioutas, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/268,114

(22) Filed: Oct. 7, 2002

(65) Prior Publication Data

US 2004/0065159 A1 Apr. 8, 2004

Related U.S. Application Data

(63) Continuation-in-part of application No. 09/992,544, filed on Nov. 13, 2001, now Pat. No. 6,829,919.

(60) Provisional application No. 60/248,330, filed on Nov. 13, 2000.

(51) Int. Cl.
*G01N 15/00* (2006.01)

(52) U.S. Cl. .................. 73/28.05; 356/335; 356/336; 356/338

(58) Field of Classification Search .... 73/28.04–28.06, 73/28.01, 865.5, 863.22; 250/288; 356/335–336, 356/338–343
See application file for complete search history.

(56) References Cited

U.S. PATENT DOCUMENTS

| 3,526,828 | A | | 9/1970 | Whitby ..................... 324/624 |
| 4,670,135 | A | * | 6/1987 | Marple et al. ......... 73/28.05 X |
| 5,279,970 | A | | 1/1994 | Patashnick et al. .... 73/28.04 X |
| 5,880,355 | A | | 3/1999 | Park et al. ................. 73/28.01 |
| 5,922,976 | A | * | 7/1999 | Russell et al. ............. 73/865.5 |
| 5,932,795 | A | * | 8/1999 | Koutrakis et al. ......... 73/28.01 |
| 6,022,390 | A | * | 2/2000 | Jakkula ....................... 55/345 |
| 6,101,886 | A | | 8/2000 | Brenizer et al. ......... 73/863.23 |
| 6,435,043 | B1 | | 8/2002 | Ferguson et al. ........ 73/863.22 |
| 6,523,393 | B1 | | 2/2003 | Linker et al. .......... 73/28.04 X |
| 6,732,569 | B2 | * | 5/2004 | Ondov et al. ............... 73/28.05 |

FOREIGN PATENT DOCUMENTS

| EP | 352126 A2 | * | 1/1990 | .............. 73/863.22 |
| EP | 473015 A2 | * | 3/1992 | ................. 250/302 |
| JP | 7-55689 | | 3/1995 | |

OTHER PUBLICATIONS

Meyer et al., "Development of a Sample Equilibration System for the TEOM Continuous PM Monitor," J. Air & Waste Manage. Assoc., vol. 50:1345-1349 (Aug. 2000).

Patashnick and Rupprecht, "Continuous PM-10 Measurements Using the Tapered Element Oscillating Microbalance," J. Air & Waste Manage. Assoc., vol. 41, 1079-1083 (Aug. 1991).

(Continued)

*Primary Examiner*—Thomas P. Noland
(74) *Attorney, Agent, or Firm*—Fish & Richardson P.C.

(57) ABSTRACT

An impactor inlet for a system for monitoring an aerosol including a plurality of particles is provided. Each of the particles has a size. The inlet includes a housing defining a chamber to receive and direct a flow of the aerosol. A high flow rate nozzle receives the aerosol at a flow rate of greater than 20 liters per minute (lpm) and accelerates and directs the aerosol flow toward a impaction plate. The aerosol flow separates into a minor flow including particles having a size greater than about 10 um, and a major flow including the remaining particles. The minor flow impacts on the impaction plate, and the major flow is emitted from an outlet.

15 Claims, 4 Drawing Sheets

OTHER PUBLICATIONS

"Development and Evaluation of a Continuous Coarse ($PM_{10}$- $PM_{2.5}$) Particle Monitor," C. Misra, , M. Geller, C. Sioutas, and P. Solomon, Journal of Air and Waste Management Association, vol. 51, pp. 1309-1317 (Sep. 2001).

"Development of Small-Cutpoint Virtual Impactors and Applications in Environmental Health," C. Sioutas and P. Koutrakis, pp. 453-470 of Advances in Aerosol Filtration (K. Spurny, ed.) (1998), month not given.

"Development of a Reference Standard for Particulate Matter Mass in Ambient Air," H. Patashnick, G. Rupprecht, J. L. Ambs, and M. B. Meyer, Aerosol Science and Technology, vol. 34, pp. 42-45 (2001), month not given.

"Evaluation of the TEOM Method for Measurement of Ambient Particulate Mass in Urban Areas," G. Allen, C. Sioutas, P. Koutrakis, R. Reiss, F. W. Lurmann, and P. T. Roberts, Air & Waste Management Assoc., vol. 47, pp. 682-689 (Jun. 1997).

"Versatile Aerosol Concentration Enrichment System (VACES) for Simultaneous in vivo and in vitro Evaluation of Toxic Effects of Ultrafine, Fine and Coarse Ambient Particles Part I: Development and Laboratory Characterization," S. Kim, P. A. Jaques, M. Chang, J. R. Froines, and C. Sioutas, Aerosol Science, vol. 32, pp. 1281-1297 (2001), month not given.

* cited by examiner

FIG. 6

```
                62              64              66
                ┌─────────┐    ┌─────────┐    ┌──────┐
   AIR ────────▶│ VIRTUAL │───▶│  INLET  │───▶│ TEOM │
                │IMPACTOR │    │IMPACTOR │    └──────┘
                └────┬────┘    └────┬────┘
                 68   70            │
                     ▼              ▼
                                 EXHAUST
```

70 — RECEIVING AN AREOSOL AT AN INLET FLOW RATE

↓

72 — REMOVING A FIRST RANGE OF PARTICLE SIZES

↓

74 — REMOVING A SECOND RANGE OF PARTICLE SIZES

↓

76 — EMITTING THE REMAINING PORTION OF THE AEROSOL AT AN OUTLET FLOW RATE

↓

78 — MEASURING A CHARACTERISTIC OF THE REMAINING FLOW OF AIR

US 6,990,846 B2

IMPACTOR INLET

CROSS REFERENCE TO RELATED APPLICATIONS

This application is a continuation-in-part of and claims the benefit of priority under 35 U.S.C. § 120 of U.S. application Ser. No. 09/992,544, filed Nov. 13, 2001, now issued as U.S. Pat. No. 6,829,919, which claims priority from U.S. Provisional Application Ser. No. 60/248,330, filed Nov. 13, 2000. The disclosure of application Ser. No. 09/992,544 is considered part of (and is incorporated by reference in) the disclosure of this application.

STATEMENT AS TO FEDERALLY-SPONSORED RESEARCH

This invention was made with government support under Control No. 2155-G-AB805 awarded by the Environmental Protection Agency. The government has certain rights in the invention.

TECHNICAL FIELD

This invention relates to particulate matter monitors, and more particularly to inlets for monitoring of particulate matter.

BACKGROUND

Since the advent of the particulate matter (PM) standards by the United States Environmental Protection Agency (US EPA), particle sampling has become a primary goal of both scientists and lawmakers. The addition of the PM2.5 (fine particle) and the soon to be developed PM10-PM2.5 (coarse particle) standards to the PM10 standard has created a need for reliable continuous coarse and fine PM measurement devices.

An essential component of a modern PM monitoring device is a size pre-selective inlet. This is even more important when the size range to be removed prior to sampling consists of large particles. If the inlet allows even a small fraction of the undesirable PM into the measuring device, the error could be large. The reason for this is that large particles have large masses, which may heavily influence the measurement of a mass-based monitor.

Because of their large mass, hence inertia, coarse particles are difficult to sample and collect. When these heavy particles are accelerated in an impactor jet, their substantial inertia causes them to hit the impactor collection plate. Many times the particle will bounce off this plate and become re-entrained in the air stream. This may cause overestimation of the mass downstream of the inlet. Re-entrainment of particles may also be related to the flow rate of the aerosol flowing into the inlet. As the flow rate increases, re-entrainment increases.

Another problem that occurs because of the inertia of these particles is the underestimation of particle mass that results from anisokinetic sampling. Anisokinetic sampling is a condition in which the mean velocity of the flowing air differs from the mean velocity of the air entering the inlet of the sampling probe. In addition, unlike the PM in smaller size ranges, coarse PM is not as uniformly dispersed in the atmosphere. It settles and becomes resuspended due to localized events (i.e. high wind episodes).

SUMMARY

In one aspect, an impactor inlet for a system for monitoring an aerosol including a plurality of particles is provided. Each of the particles has a size. The inlet includes a housing defining a chamber to receive and direct a flow of the aerosol. A high flow rate nozzle receives the aerosol at a flow rate of greater than 20 liters per minute (lpm) and accelerates and directs the aerosol flow toward a impaction plate. The aerosol flow separates into a minor flow including particles having a size greater than about 10 um, and a major flow including the remaining particles. The minor flow impacts on the impaction plate, and the major flow is emitted from an outlet.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 is a block diagram of an embodiment of a system for monitoring an aerosol.

FIG. 7 is a flow diagram of a process for monitoring an aerosol.

Like reference symbols in the various drawings indicate like elements.

DETAILED DESCRIPTION

Figure 1:
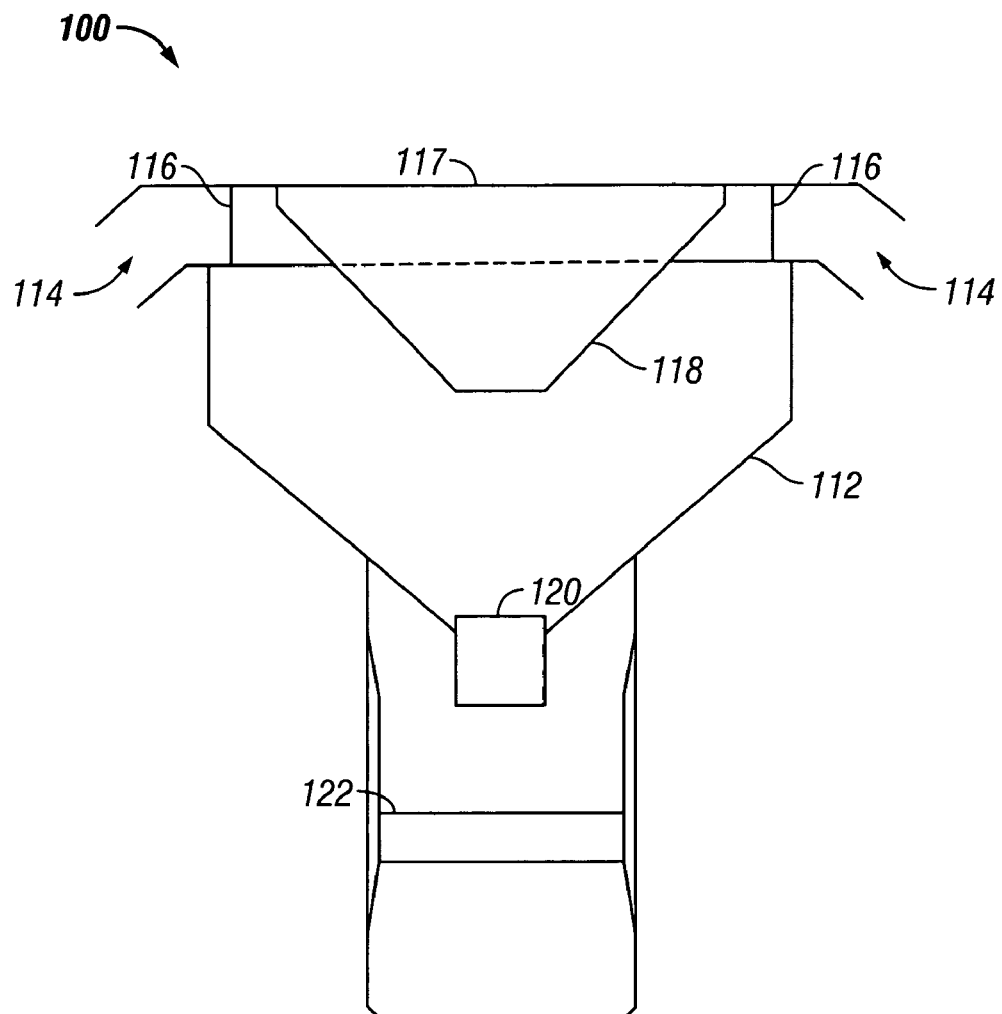
FIG. 1 is a two-dimensional perspective view of an aspect of an impactor inlet.

FIG. 1 shows an aspect of a high flow rate inlet 100 for receiving an aerosol containing particulate matter. The high flow rate inlet 100 is configured to receive the aerosol at a flow rate of about 50 lpm and to have a high efficiency cutpoint. The high flow rate inlet 100 may separate the particulate matter as a function of size. For example, particulate matter having an aerodynamic diameter that is greater than or equal to 10 um may be separated from particulate matter having an aerodynamic diameter that is less than 10 um. The smaller diameter particulate matter may then be passed through the impactor inlet 100 to a monitoring device.

The high flow rate inlet 100 includes a housing 112 to provide an enclosure and to direct the flow of the aerosol. An air intake 114 in the housing 112 receives the aerosol into the high flow rate inlet 100 and is configured to reduce anisokinetic sampling errors. The air intake 114 may comprise an opening extending about the circumference of the housing so that air may flow into the housing from any direction. The opening may be discontinuous so long as air from substantially all directions may be received into the housing 112. One such air intake 114 may be located along a vertical surface of the housing beneath an upper surface 117. An insect screen 116 may optionally be provided at the air inlet 114 to prevent insects from contaminating the aerosol.

A deflection cone 118 may redirect the aerosol towards a nozzle 120. The deflection cone 118 provides one alternative for receiving an aerosol from a sidewardly facing air intake while directing the aerosol flow in a downward direction.

Figure 2:
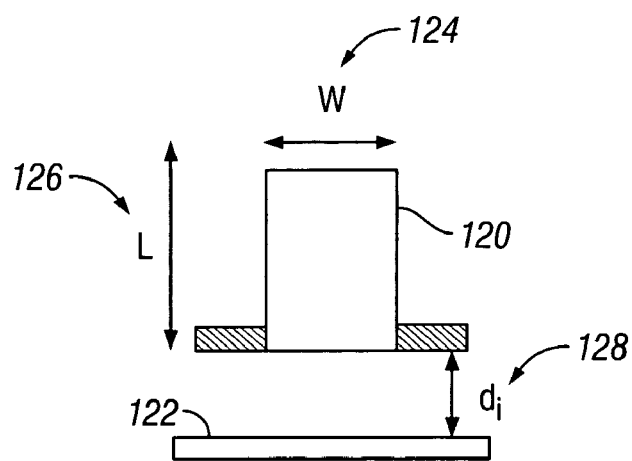
FIG. 2 is a two-dimensional perspective view of an aspect of an impactor inlet nozzle.

A nozzle 120 receives the flow of aerosol and concentrates and directs that flow towards an impaction plate 122. FIG. 2 shows an expanded view of the nozzle 120 in relation to the impaction plate 122. The nozzle 120 preferably has a cutpoint of about 10 um at a flow rate of about 50 lpm. However, the nozzle may include other cutpoints ranging from 0.25 um. Conventional nozzles that have a cutpoint of 10 um are generally limited to a flow rate of 16.7 lpm. The invention recognizes that to attain a higher flow rate while maintaining a sharp cutpoint at 10 um, the nozzle diameter, W, 124 may be widened, the nozzle length, L, 126 may be shortened, and the distance, 128 from the jet-to-impaction plate may be increased. For example, in one embodiment, the nozzle 120 may have a diameter 124 of about 1.7 cm, a length 126 of about 4.7 cm, and a distance 128 to the impaction plate of about 1.1 cm.

To determine a figure of merit for particle capture, the Stokes number, $S_t$, of a particle having a 50% probability of impacting may be computed. The Stokes number is defined as follows:

$$St = \frac{\tau U}{W} = \frac{\rho_p C_c d_p^2 U}{9\mu W}$$

where U is the jet velocity, t is the relaxation time, W is the nozzle diameter, $p_p$ is the particle density, u is the dynamic viscosity of the air, $d_p$ is the particle diameter in um, and $C_c$ is the Cunningham slip correction factor.

$$C_c = 1 + \frac{2}{Pd_p}\left[6.32 + 2.01\exp^{(-0.1095Pd_p)}\right]$$

where P is the absolute pressure in the impaction region (in cm Hg) and the corresponding jet velocity for a flow rate of 50 lpm is 367 cm/s. The computed Stokes number corresponding to a cut-point of 10 um and the exemplary nozzle is about 0.16.

Figure 3:
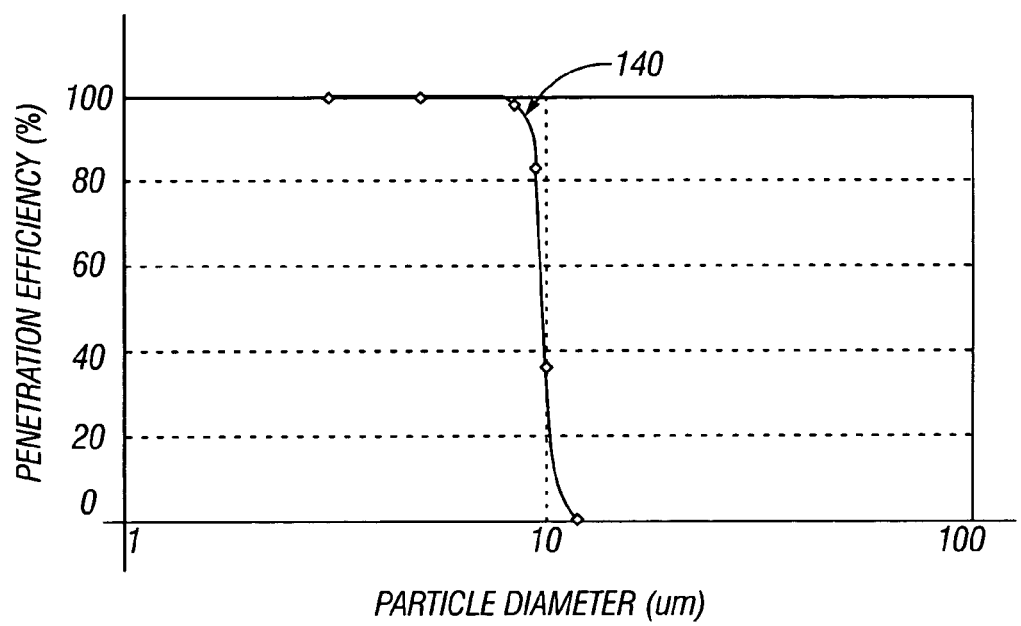
FIG. 3 is a graph showing penetration distance versus particle diameter.

FIG. 3 shows a graph of the efficiency of one aspect of a high flow rate inlet in accordance with the principles described herein. A waveform 140 of the penetration efficiency versus aerodynamic diameter shows that particle penetration may be 90% or higher for particles in the range of 2.5 to 8 um. Penetration decreases sharply to about 50% at 9.5–9.7 um and further to less than 10% for particles larger than 11 um in aerodynamic diameter. A geometric standard deviation (σg) may be determined, to use as an estimate of the sharpness of the particle penetration. This may be used to indicate very sharp aerodynamic particle separation characteristics ($\sigma_g$=1.1) for the high flow rate inlet.

Figure 4:
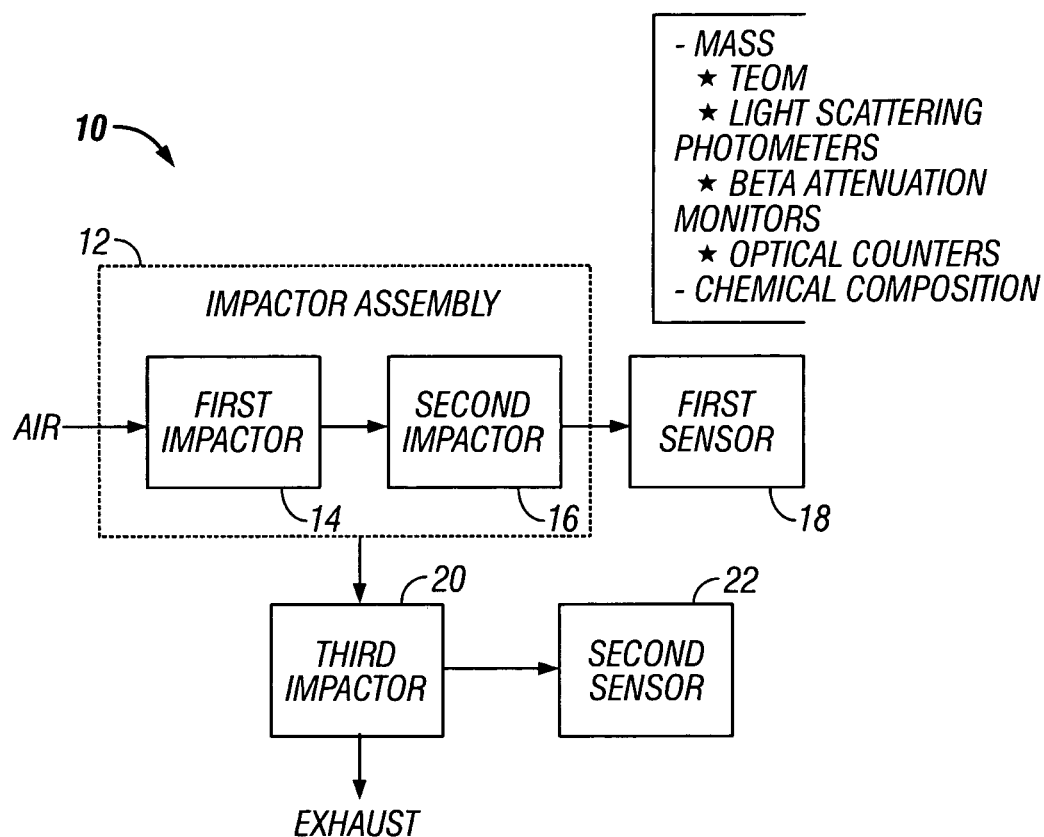
FIG. 4 is a block diagram of an embodiment of a system for monitoring an aerosol.

FIG. 4 shows an aspect of a particulate matter monitor 10 that includes an aspect of the above described high flow rate inlet. The monitor 10 is particularly suitable for continuous monitoring of coarse particulate matter having an aerodynamic diameter of 2.5 um to 10 um. However, the monitor 10 may be used to monitor aerosols that include particulate matter having other size ranges including aerodynamic diameters between 0.25 um to 100 um. The monitor system 10 includes an impactor assembly 12 coupled to a first sensor 18. The impactor assembly 12 removes particles having an aerodynamic diameter outside of a predetermined band such as the band between 2.5 um to 10 um. The impactor assembly 12 includes a first impactor 14 and a second impactor 16 connected in series. At least one of the impactors 14 and 16 includes an high flow rate inlet for receiving the aerosol at a flow rate of about 50 lpm. Each of the impactors 14 and 16 removes a band of particles based upon the size of the particles. For example, the first impactor 14 may remove particles having an aerodynamic diameter greater than 10 um, and the second impactor 16 may remove particles having an aerodynamic diameter less than a minimum particle size. The remaining portion of the particles in the aerosol have an aerodynamic diameter predominantly in the range between the minimum and maximum particle size, although there may be a minimal quantity of particles within the remaining portion that may have an aerodynamic diameter outside the range of 2.5 um to 10 um.

The impactors 14 and 16 may also concentrate the quantity of particles having a particle size between the minimum and maximum particle size so that an enriched aerosol is supplied to the first sensor 18. The particles may be concentrated by receiving an aerosol into the impactor assembly 12 at an inlet flow rate, and supplying the enriched aerosol to the first sensor 18 at an outlet flow rate that is less than the inlet flow rate. The level of concentration is a function of the ratio of the inlet flow rate to the outlet flow rate. For example, at an inlet flow rate of 50 lpm and an outlet flow rate of 2 lpm, a remaining portion of particles in a band between the minimum and maximum particle size may be concentrated by a factor of about 25 while maintaining the quantity of particles that are less than the minimum particle size at about ambient concentrations.

The first sensor 18 receives the enriched aerosol from the impactor assembly 12 and continuously measures a predetermined characteristic of the particles in the aerosol. The first sensor 18 may measure particle characteristics including mass and chemical composition. Devices that may be used for measuring mass include tapered element oscillating microbalances (TEOMs), light scattering photometers, beta attenuation monitors, and optical counters. For measuring chemical composition, devices include ion chromatographs for sulfate, nitrate, sodium, and ammonium; inductively-coupled plasma mass spectrometers and graphite furnaces for trace elements and metals; thermal desporption units for organic concentrations; and mass spectrometers for detection of biologically active compounds in airborne coarse particles.

A third impactor 20 may be coupled to the impactor assembly 12 to extract another band of particle sizes to be measured by another sensor 22. The third impactor 20 may be arranged to receive a portion of the aerosol that includes particles having an aerodynamic diameter that is either less than the minimum particle size or greater than the maximum particle size. The third impactor 20 removes another portion of the particles based upon particle size so that the remaining portion includes particles having sizes within a another band of particle sizes such as between the minimum particle size and a smaller particle size that is less than the minimum particle size. For example, the impactor assembly 12 may remove particles having sizes outside the range of 2.5 um to 10 um. The third impactor 20 may then receive the exhaust aerosol from the impactor assembly 12 including particles having sizes that are less than 2.5 um. The third impactor 20 may remove particles from the exhaust aerosol having particle sizes that are less than 1.5 um. A remaining portion of the aerosol having particles with sizes in the range of 1.5 um to 2.5 um is sent to the second sensor 22 to be measured. In addition, the third impactor 20 may concentrate the particles having the selected range of sizes by emitting the aerosol at an outlet flow rate that is less than the flow rate into the third impactor 20. Further fractionate portions of the particles may be obtained by coupling further impactors and sensors to the third impactor 20 or to the impactor assembly 12.

Figure 5:
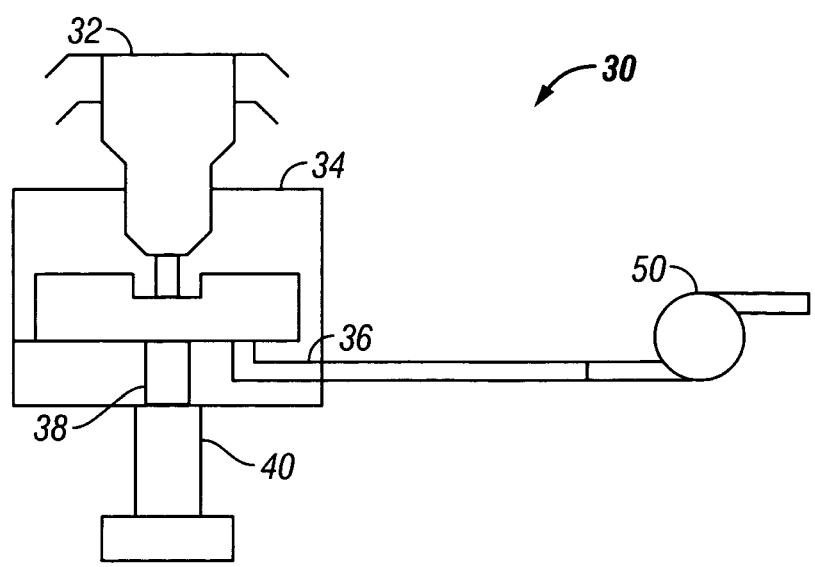
FIG. 5 is a two-dimensional diagram of a system for monitoring an aerosol.

FIG. 5 shows a two-dimensional view of an embodiment of a particulate matter (PM) monitor 30 for measuring a characteristic of PM. The PM is suspended in an aerosol that is drawn into a high flow rate inlet 32 at about 50 lpm. The high flow rate inlet 32 removes matter that has an aerodynamic diameter that is greater than 10 um. A first virtual impactor 34 is coupled to the high flow rate inlet 32 to remove particles that have an aerodynamic diameter that is less than 2.5 um. The first virtual impactor 34 has a major flow 36 with a flow rate of 48 lpm, and a minor flow 38 with a flow rate of 2 lpm. The major flow 36 includes the particles that have a size that is less than 2.5 um. The minor flow 38 includes an enriched aerosol of the particles ranging in size between 2.5 um and 10 um. The concentration of the selected particles is about 25 times the ambient level. The enriched aerosol additionally includes an ambient level of particles having a size that is less than 2.5 um. The minor flow 38 is coupled to a TEOM 40 that measures the mass of the PM.

The major flow 36 is coupled to a pump 50 that draws the aerosol through the PM inlet 32 and the virtual impactor 34. Alternatively, the major flow 36 may be coupled to a second virtual impactor (not shown) to extract a fractionate portion of particles from the first virtual impactor major flow 36. The pump 50 would then be coupled to the second virtual impactor.

FIG. 6 shows another embodiment of a PM monitor 60 for measuring a characteristic of PM. The configuration of the PM monitor 60 is similar to PM monitor 30 except that the aerosol is drawn into a virtual impactor 62 before flowing through a high flow rate inlet impactor 64 and into a sensor 66. The aerosol is drawn into the virtual impactor 62 at an inlet flow rate. A major flow 68 of the virtual impactor 62 exhausts particles that are smaller than a minimum particle size. A minor flow 70 of the virtual impactor 62 outputs an enriched aerosol at an outlet flow rate that is less than the inlet flow rate. The enriched aerosol includes particles that have an aerodynamic diameter that is greater than the minimum particle size. The particles are concentrated at a level above the ambient level by a factor approximately equal to the ratio of the inlet flow rate to the outlet flow rate of the virtual impactor 62. The inlet impactor 64 removes particles from the enriched aerosol that have a particle size that is greater than the maximum particle size. The remaining portion of the aerosol includes an enriched portion containing particles ranging in size between the minimum particle size and the maximum particle size, as well as an ambient level of particles that are less than the minimum particle size.

FIG. 7 shows a flow chart for a PM measurement process. Starting at block 70, an aerosol including PM is drawn into a high flow rate inlet at an inlet flow rate equal to or greater than 20 lpm. Continuing at block 72, a first portion of particles having particle sizes in a first range is removed from the aerosol. At block 74, another portion of particles having particle sizes in a second range is also removed from the aerosol so that the remaining portion has particles that have particle sizes between a minimum particle size and a maximum particle size. Continuing to block 76, the remaining portion of the aerosol is emitted at an outlet flow rate that is less than the inlet flow rate so that the particles between the minimum particle size and the maximum particle size are concentrated in the remaining aerosol. Finishing at block 78, measuring a characteristic of the remaining aerosol.

A number of embodiments of the invention have been described. Nevertheless, it will be understood that various modifications may be made without departing from the spirit and scope of the invention. Accordingly, other embodiments are within the scope of the following claims.

What is claimed is:

1. A system for monitoring an aerosol including a plurality of particles, each of the particles having a size, comprising:
    a high flow rate inlet operable to receive a flow that includes the aerosol at an inlet flow rate greater than 20 liters per minute and to remove particles having sizes greater than about 10 um from the flow, a remaining portion of the particles being emitted in the flow, the inlet including a nozzle assembly having an impaction plate to remove the particles from the flow;
    a first impactor to receive and separate the remaining portion of the particles into a first portion and a second portion, the first portion including particles having sizes less than a minimum particle size, the second portion including particles having sizes at least equal to the minimum particle size; and
    at least a first sensor to measure a characteristic of the second portion of the particles.

2. The system of claim 1 wherein the minimum particle size is about 2.5 um.

3. The system of claim 1 wherein the characteristic of the second portion of the particles is selected from the group consisting of mass and chemical composition.

4. The system of claim 1 wherein the sensor includes a tapered element oscillating microbalance (TEOM).

5. The system of claim 1 wherein the sensor is selected from the group consisting of a TEOM, light scattering photometers, a beta attenuation monitors, optical counters, ion chromatographs, inductively-coupled plasma mass spectrometers, graphite furnaces, thermal desorption units, and mass spectrometers.

6. The system of claim 1 further comprising a pump to pull the aerosol into the high flow rate inlet.

7. The system of claim 1 wherein the second portion of particles has a second flow rate; and
    a ratio of the inlet flow rate to the second flow rate is in a range from 2 to 50.

8. The system of claim 1 further comprising a second impactor including a first virtual impactor to receive the first portion of the particles and to remove particles less than a first particle size, a first flow of the first virtual impactor to emit a portion of the particles at least equal to the first particle size.

9. The system of claim 8 wherein the first particle size is about 1.0 um.

10. The system of claim 8 wherein the second impactor includes a second virtual impactor to remove a portion of the particles greater than a second particle size, a first flow of the second virtual impactor to emit a remaining portion of the particles.

11. The system of claim 1 wherein the nozzle assembly includes a nozzle and is dimensioned in accordance with $$St = \frac{\tau U}{W} = \frac{\rho_p C_c d_p^2 U}{9\mu W}$$

where U is a jet velocity, t is a relaxation time, W is a nozzle diameter, $p_p$ is a particle density, u is the dynamic viscosity of the air, $d_p$ is a particle diameter in um, and $C_c$ is the Cunningham slip correction factor which is given by $$C_c = 1 + \frac{2}{Pd_p}\left[6.32 + 2.01\ \exp^{\left(-0.1095P_{d_p}\right)}\right]$$

where P is absolute pressure (in cm Hg) in an impaction region of the nozzle assembly.

12. The system of claim 1 wherein the high flow rate inlet is operable to receive a flow that includes the aerosol at an inlet flow rate of about 50 lpm.

13. The system of claim 12 wherein:

the nozzle assembly further comprises a nozzle having a diameter perpendicular to flow through the nozzle of about 1.7 cm and a length in the direction of the flow through the nozzle of about 4.7 cm; and a distance between the impaction plate and the nozzle is about 1.1 cm.

14. The system of claim 1 wherein the high flow rate inlet comprises:

a housing; and a circumferential opening in the housing to allow air from substantially all directions to enter the housing.

15. The system of claim 14 wherein the high flow rate inlet further comprises a deflection cone disposed within the circumference defined by the circumferential opening to deflect the air from substantially all directions in a same direction.

* * * * *